(12) United States Patent
Russo

(10) Patent No.: US 6,923,184 B1
(45) Date of Patent: Aug. 2, 2005

(54) SUCTION SYSTEM WITH HIGH EFFICIENCY SUCTION CONTROL VALVE

(76) Inventor: Ronald D. Russo, 8 Candleberry Rd., Barrington, RI (US) 02806

( * ) Notice: Subject to any disclaimer, the term of this patent is extended or adjusted under 35 U.S.C. 154(b) by 38 days.

(21) Appl. No.: 10/058,540

(22) Filed: Jan. 28, 2002

Related U.S. Application Data

(60) Provisional application No. 60/305,774, filed on Jul. 17, 2001, provisional application No. 60/271,481, filed on Feb. 27, 2001, provisional application No. 60/266,200, filed on Feb. 5, 2001.

(51) Int. Cl.[7] .......................... A61M 16/00; A62B 9/06
(52) U.S. Cl. ........................ 128/207.14; 128/200.26; 128/205.12; 128/207.16
(58) Field of Search ............... 128/200.26, 205.12, 128/207.14, 207.16; 604/35, 118, 171, 265, 604/250, 163, 119; 137/381

(56) References Cited

U.S. PATENT DOCUMENTS

| | | | | |
|---|---|---|---|---|
| 4,193,406 A | * | 3/1980 | Jinotti | 128/204.18 |
| 4,569,344 A | * | 2/1986 | Palmer | 128/207.16 |
| 5,215,522 A | * | 6/1993 | Page et al. | 604/33 |
| 5,254,098 A | * | 10/1993 | Ulrich et al. | 604/171 |
| 5,279,549 A | * | 1/1994 | Ranford | 604/34 |
| 5,300,043 A | * | 4/1994 | Devlin et al. | 604/250 |
| 5,325,850 A | * | 7/1994 | Ulrich et al. | 128/200.26 |
| 5,349,950 A | * | 9/1994 | Ulrich et al. | 128/207.16 |
| 5,377,672 A | * | 1/1995 | Kee | 128/207.16 |
| 5,460,613 A | * | 10/1995 | Ulrich et al. | 604/118 |
| 5,490,503 A | * | 2/1996 | Hollister | 128/205.12 |
| 5,496,287 A | * | 3/1996 | Jinotti | 604/249 |
| 5,598,840 A | * | 2/1997 | Iund et al. | 128/207.14 |
| 5,676,136 A | * | 10/1997 | Russo | 128/205.24 |
| 5,720,282 A | * | 2/1998 | Wright | 128/207.14 |
| 5,730,123 A | * | 3/1998 | Lorenzen et al. | 128/207.14 |
| 5,730,727 A | * | 3/1998 | Russo | 604/118 |
| 5,738,091 A | * | 4/1998 | Kee et al. | 128/205.12 |
| 5,775,325 A | * | 7/1998 | Russo | 128/205.12 |
| 5,779,687 A | * | 7/1998 | Bell et al. | 604/265 |
| 6,012,451 A | * | 1/2000 | Palmer | 128/200.26 |
| 6,070,582 A | * | 6/2000 | Kee | 128/207.16 |
| 6,588,425 B2 | * | 7/2003 | Rouns et al. | 128/207.14 |

* cited by examiner

*Primary Examiner*—Glenn K. Dawson
*Assistant Examiner*—Michael Mendoza
(74) *Attorney, Agent, or Firm*—Robert J Doherty

(57) ABSTRACT

An improved trachea suction system includes a suction catheter with a high efficiency suction control valve providing unobstructed fluid flow in its activated suction applied mode for removal of viscous secretions at a low level of applied input suction through the catheter. The valve also non-restrictive to air flow at the distal tip of the catheter. The valve ideally part of a closed tracheal suction system having a catheter isolator seal with a vortex action catheter cleaning chamber located in front of the isolator seal which takes advantage of the high efficiency characteristics of the suction control valve.

20 Claims, 8 Drawing Sheets

SUCTION SYSTEM WITH HIGH EFFICIENCY SUCTION CONTROL VALVE

RELATED APPLICATIONS

The inventor clam the fill benefit of the following U.S. Provisional Patent Applications: "Transverse Closed Tracheal Suction Device" filed Feb. 5, 2001, application No. 60/266,200; "Compact Closed Trahceal Suction Device" filed Feb. 27, 2001, application No. 60/271,481; and "High Efficiency Suction Control Valve" filed Jul. 17, 2001, application No. 60/305,774.

BACKGROUND OF THE INVENTION

This invention relates to suction catheter systems with suction control valves especially those used in medical applications. Suction catheters are used to remove secretions from a patient's airway and catheters fall into two categories of single use disposable: "Open" style catheters and the newer type "closed" systems manufactured by Ballard Medical Inc. and SIMS Portex.

"Open" style catheters typically use a normally open suction control valve such as those described in U.S. Pat. No. 4,534,542 to Russo. The "closed" tracheal suction systems typically use a normally closed suction control valve as described in U.S. Pat. No. 4,569,344 to Palmer, U.S. Pat. No. 4,696,296 also to Palmer, and U.S. Pat. No. 5,073,164 to Hollister. The closed systems usually comprise a frontal connector attachable to a ventilator and the patient's endotracheal tube along with a protective sleeved suction catheter and a normally closed suction control valve. The valve must be normally closed to prevent the loss of administered ventilation when the patient is not being suctioned since the closed system is left attached to the patient and the breathing circuit at all times.

The normally closed valves described in the above patents (Palmer and Hollister) are actually in commercial use as part of the Ballard Medical Trach-Care® product and the SIMS Portex Steri-Cath® and they suffer from several limitations which impact their clinical efficacy and their low suction efficiency. As noted, the valves used in both the Ballard Medical and SIMS Portex devices are 100% obstructed when they are positioned in their non-activated, non-suction applied mode. However, they remain in a partially blocked or partially obstructed flow path position when they are activated in their suction applied mode. This means that suction levels have to be set exceedingly high in order to equal the suction efficiency of the open straight through flow paths of the open style catheters. Actual suction levels in an open style catheter are usually set at a clinically documented low suction level of about 125 mmHg and will efficiently remove viscous secretions with little mucosal tissue grab and trauma at that level.

By comparison, actual levels in some closed systems have to be set at 300 mmHg to approach the suction efficiency of the open style devices. Even at that level, the closed devices sometimes have difficulty removing viscous secretions due to the obstructive, restrictive flow path design of their normally closed valves which also decreases air flow at the distal tip of the catheter. Also, since the Palmer/Ballard Medical valve type has a spring action biased sealing member acting on a valve seat, the seating surface is more prone to being clogged by viscous secretions especially if the valve is not flushed well after use. Clogging of the valve seat may leave the valve partially open such that the valve may have a slow leakage of ventilated gases since it may not 100% seat closed. In addition, the Palmer/Ballard Medical valve type has many acting parts requiring more expensive manufacturing in assembly time and labor.

Towards this end, a Suction System with High Efficiency Suction Control Valve has been conceived to provide a normally closed suction control valve which is non-obstructive to both fluid and air flow in its suction applied mode and will only require the low 125 mmHg safe level of suction.

Further, closed tracheal suction devices such as the Ballard Trach-Care® and SIMS Steri-Cath® are being used for repeated suctioning and secretion removal procedures and these devices can stay connected to a patients respiratory system for up to 72 hours or 3 days. Ballard Medical has recently commercially introduced a 72 hour product (Trach-Care 72) which is the commercial embodiment of U.S. Pat. No. 6,227,200 issued to Crump et. al. and assigned to Ballard Medical Products which references many of the prior art patents. However this new Trach-Care® 72 still uses the same obstructive suction control valve used in the original Trach-Care®. Viscous secretions which may tend to partially accumulate in the frontal connector portion of closed tracheal suction devices can easily be re-introduced by the catheter during subsequent suctioning procedures which may cause VAP (ventilator associated pneumonia). Complete removal of secretions throughout the system is of paramount importance. It would be ideal to provide a high efficiency suction control valve which could be utilized as part of a closed tracheal suction system which completely isolates the catheter when not in use and which thoroughly and effectively cleans all secretions after use, and also prevents the accumulation of secretions within the system especially within the connector. Thus there is a need for a catheter apparatus which will solve all the aforementioned problems.

SUMMARY OF THE INVENTION

The ideal normally closed suction control valve would produce a high suction efficiency at a low level of applied suction of about 125 mmHg while not restricting air flow at the distal tip of the suction catheter. The present invention meets this objective for the first time in an inexpensive single patient use disposable medical device. It comprises only three injection molded parts and is very inexpensive to produce and assemble. It has a rigid ABS or PVC housing into which is inserted a synthetic molded rubber plunger which is air tight hermetically sealed into place ultrasonically by a seal ring also made from rigid ABS or PVC.

The plunger normally seals off the main suction passageway when in a non-suction applied mode. Upon manual depression of the plunger button actuator, the main central suction passageway is forced open by an upper suction cross lumen in the plunger. Manual release of the plunger automatically returns the valve to its normally closed position. The valve can be used as part of any catheter or suction tube device, but is especially applicable for use in any closed tracheal suction system.

Ideally, however, the high efficiency valve is combined and made part of a closed tracheal suction system which prevents VAP by providing for isolation of the catheter when not in use, thorough cleansing of the catheter, effective removal of any catheter secretions withdrawn and accumulated secretions within the system after catheter retraction back into the system after suctioning a patient's respiratory system is completed, and the application of a safe, low level of suction at the catheter distal tip to reduce mucosal tissue damage during suctioning.

It is therefore an object of the present invention to meet all the above objects.

It is another object of the present invention to provide a 100% normally closed air tight catheter isolator seal which can be opened or closed solely by advancement or retraction of a catheter or tube through the seal.

It is another object of the present invention to provide a single catheter wiper as part of a catheter cleaning chamber to thoroughly remove secretions from the outside of the catheter and to deposit those secretions in the catheter cleaning chamber distal to the wiper.

It is a further objective to provide an air flow vortex action catheter cleaning chamber which effectively removes accumulated secretions from the catheter cleaning chamber and the ventilator connector.

It is a further objective to provide a single combination bronchial lavage and catheter rinse port which accesses the catheter cleaning chamber.

It is a further objective to utilize the efficiency of the high efficiency suction control valve to remove tracheal secretions within the airway at a low level of input suction to prevent mucosal tissue damage.

It is a further objective to utilize the efficiency of the high efficiency suction control valve to clean the catheter prior to retraction into a catheter isolator tunnel.

In accordance with another aspect of the present invention a replaceable catheter cartridge is provided such that the frontal connector which incorporates the catheter cleaning chamber and isolator seal can remain connected to the patient without losing ventilator gases or PEEP when the catheter cartridge is replaced.

BRIEF DESCRIPTIONS OF THE INVENTION

Figure 1:
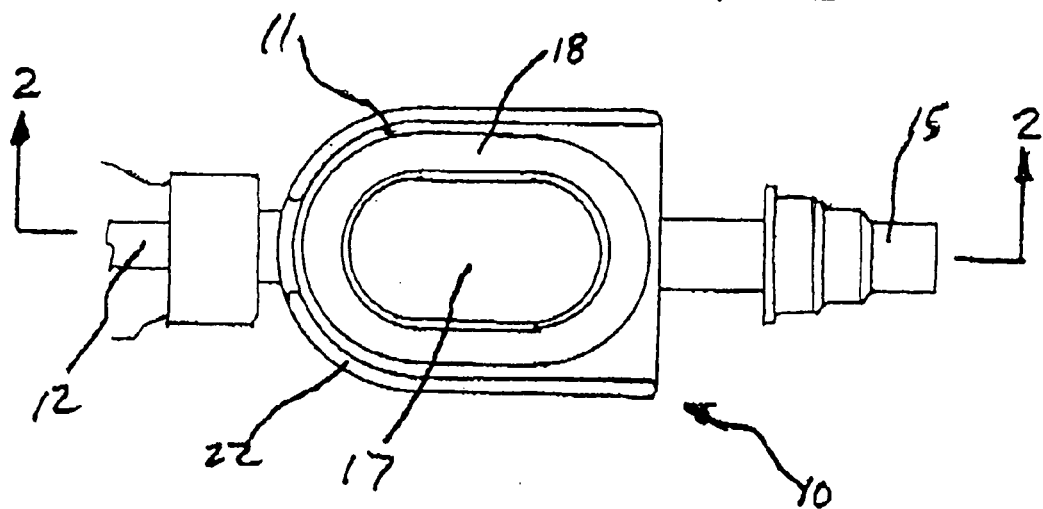
FIG. 1 is a top view of the high efficiency suction control valve.
Figure 2:
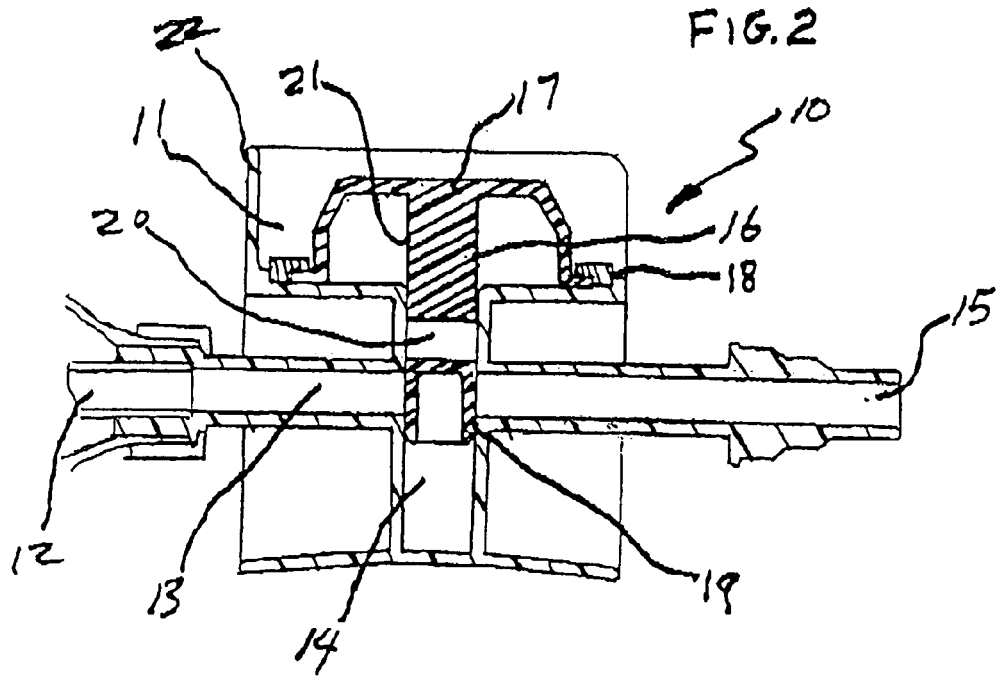
FIG. 2 is a side cross sectional view of the high efficiency taken along lines 2—2 in FIG. 1 showing the device positioned in its normally closed non-suction applied mode.

FIGS. 1 and 2 clearly show the suction control valve 10 in its normally positioned closed non-suction applied mode. Valve 10 has a one piece rigid injection molded housing 11 made from ABS or PVC plastic which can solvent cement to any catheter 12. Housing 11 has a main first central linear straight through fluid and air flow passageway 13 which is in straight line communication with catheter 12. Transversing passageway 13 is transverse second passageway 14. Passageway 13 extends past second passageway 14 rearward to built in suction connector 15 which permits direct connection to any source of regulated vacuum or suction via suction tubing. Inserted into second transversing passageway 14 is synthetic rubber molder plunger 16 which is typically circular in cross section and also has a top resiliently manually depressively activated button actuator portion 17 oval in shape. Hermetically sealing plunger 16 and actuator portion 17 in place and forming an air tight seal is seal ring 18 which is made from rigid molded ABS or PVC plastic and ultrasonically seals plunger 16 and actuator portion 17 such that they are completely sealed off from atmosphere. Plunger 16 has a lower piston 19 integrally formed which just does not block but hermetically seals off central linear passageway 13 in an air tight manner. Plunger 16 and piston 19 have slightly oversized side walls 21 which resiliently expand outward to form a 100% leak proof air tight hermetic seal within central passageway 13 and further act to seal off any leakage of suction or secretions out the valve 10 even if the valve 10 is left attached to a source of vacuum or suction such as leaving the valve connected to suction tubing. Partially running around the periphery of actuator portion 17 and part of housing 11 is built in guard flange 22 formed as part of housing 11 which is slightly higher in height than actuator portion 17. This guard flange 22 permits inadvertent depression or activation of actuator portion 17 if a patient were to roll over on top of valve 10. This guard flange 22 acts as a safety feature.

Figure 3:
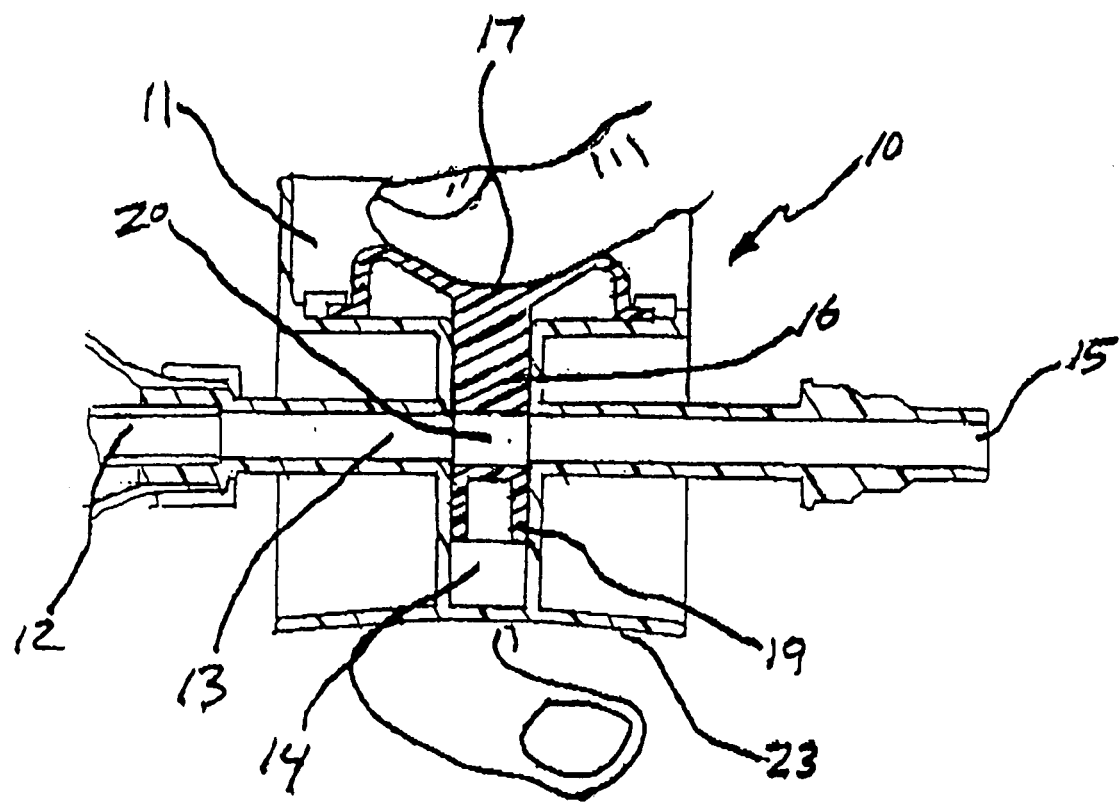
FIG. 3 is a side cross sectional view of the high efficiency suction control valve showing the device positioned in its fully open suction applied mode.

FIG. 3 is a cross sectional side view of valve 10 shown in its suction applied mode versus its non-suction applied mode depicted in FIG. 2. When manually depressed actuator portion 17 is resiliently deformed and flexed downward to slideably move plunger 16 and piston 19 downward within second passageway 14 such that cross lumen 20 will align itself and fully and completely open up central passageway 13 permitting unobstructed and unrestrictive fluid and air flow to take place through central passageway 13.

When vacuum or suction is applied by depressing actuator 17 aspirated secretions will flow through catheter 12, on through passageway 13, through cross lumen 20 in plunger 16 and out through connector 15 in an unobstructed unrestrictive manner from catheter 12 straight through valve 10 and out through the suction source. A clinically safe and desirable low level of only 125 mmHg is all that is need to move the most viscous of secretions through valve 10 since there is no obstruction to either fluid or air flow through the valve 10. The valve can also take fill advantage of the suction input air flow rate which will substantially increase suction efficiency to its highest level.

Housing 11 is provided with molded in lower finger rest 23 as shown. A very slight amount of silicone stop cock grease can be applied to plunger 16 prior to assembly into transverse second passageway 14 to act as an anti-fiction lubricant for smooth up and down slideable action of plunger 16 and piston 19 in passageway 14.

Manual release of actuator portion 17 will automatically return plunger 16 to its original normally closed sealed non-suction applied mode position as shown in FIG. 2.

In use actuator portion 17 can be depressed either continuously or intermittently when suction needs to be applied. Also actuator portion 17 is shown in an oval configuration such that the insertion of plunger 16 into transverse passageway 14 will automatically orient cross lumen 20 in its proper aligned relationship with second transverse passageway 14 and central passageway 13 providing a straight through linear internal smooth laminar flow path unlike the prior art devices which have distorted tortuous disruptive flow paths which impede, obstruct, and restrict the flow of viscous secretions to cause the secretions to block and build up.

Figure 4:
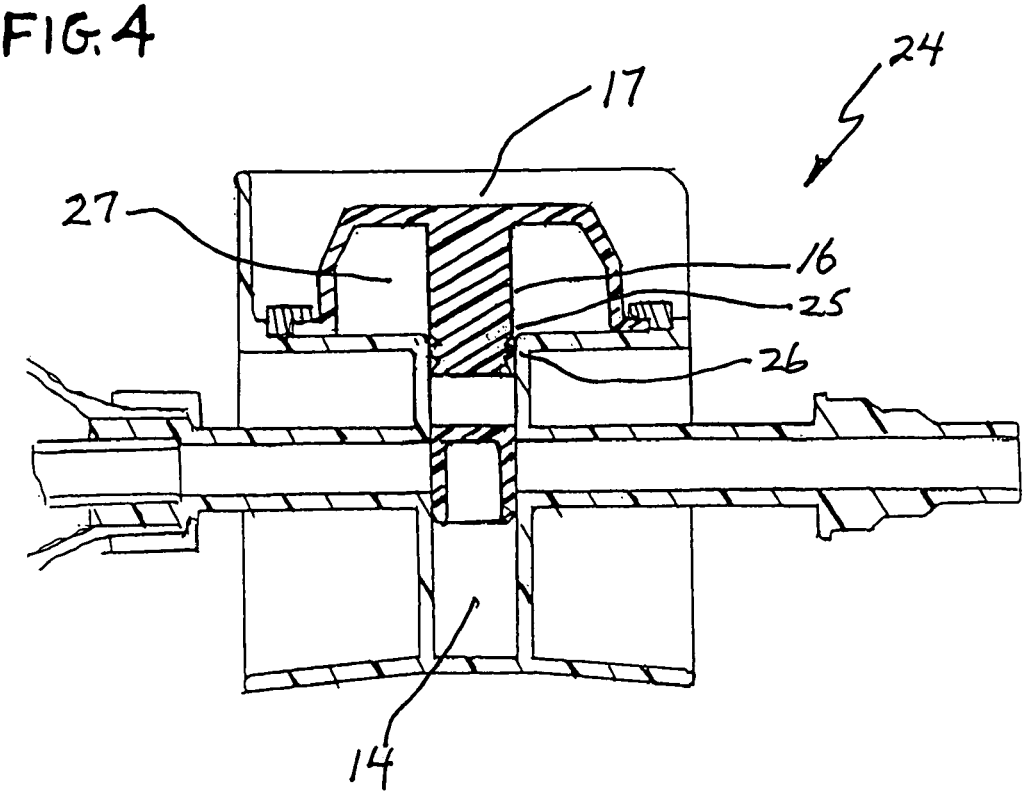
FIG. 4 is a side cross sectional view of an alternate embodiment of the high efficiency showing a molded in "O" ring wiper seal as part of the upper plunger.

In essence the oval shape automatically keys in the plunger 16 into its proper alignment with respect to passageways 13 and 14 such that it can only be assembled in manufacturing in its correct foolproof manner. In summary the valve 10 provides all the efficiencies and advantages of an open style valve only in a normally closed valve made from three simple injection molded components which can be rapidly manufactured and assembled into a finished suction control valve at low cost. Unlike the obstructive spool valves of Palmer and Hollister as well as all the other known prior art valves the present valve invention provides the highest degree of suction efficiency in a normally closed suction control valve as part of a suction system. While there is shown oval button actuator and round plungers many other configurations such as square plungers and rectangular actuators could be designed and used without departing from the broad scope from the underlying suction control valve invention FIG. 4 shows alternate embodiment 24 essentially identical to suction control valve 10 depicted in FIG. 2 with the exception that plunger 16 has upper stem portion 25 which has a built in molded wiper seal "O" ring 26 as part of plunger 16 which acts to prevent any secretions from entering in chamber 27 under button actuator 17.

Figure 5:
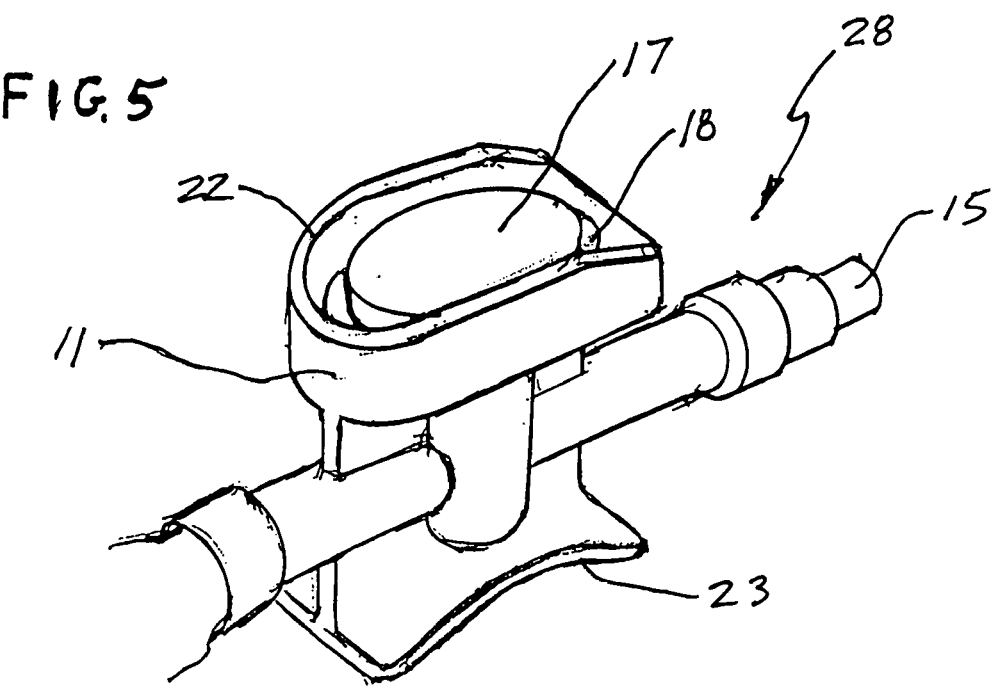
FIG. 5 is a perspective view of the high efficiency suction control valve.

FIG. 5 shows a clear perspective 28 of the valve depicted in FIG. 2 with all the main externally visible portions identified.

Figure 6:
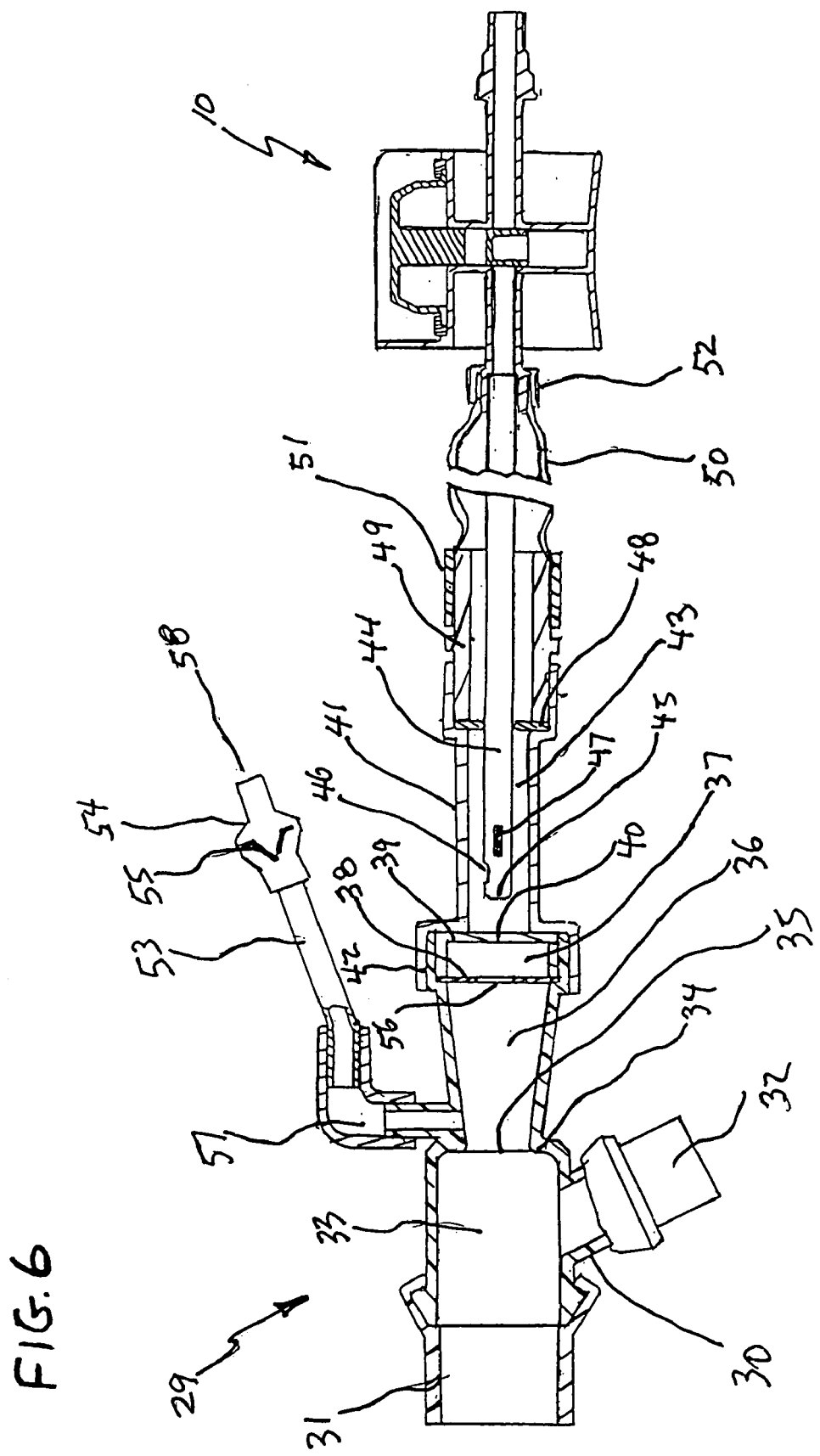
FIG. 6 is a side cross sectional view of a complete closed tracheal suction system which uses the high efficiency suction control valve.

FIG. 6 clearly depicts the closed tracheal suction system 29 of the present invention which uses valve 10 as part of its assembly and comprises frontal connector 30 with a frontal swivel 31 which directly attaches to a patient tracheal tube and a side swivel 32 for connection to the ventilator circuit for the delivery of ventilator gases into inner air passage 33 which in turn delivers gases through front swivel 31 into the tracheal tube and respiratory system of a patient. Rearward of passage 33 is wall 34 having a somewhat narrowed entrance opening 35 which opens up into larger funnel shaped catheter cleaning chamber 36. Located just behind narrowed opening 35 is a single combination lavage/flush access port 57 which is solvent bonded onto chamber 36. All the elements formed as part of connector 30 are injection molded of clear rigid ABS or PVC. Further rearward of chamber 36 is collar recess 37. Passage 33, chamber 36, and collar recess 37 are formed as one unitized plastic piece which is clear. Fitted into recess 37 is thin walled silicone catheter wiper 38 having an undersized wiper circular hole 56 dimensioned to give a wiper contact fit with all sized catheters from 10 fr up to 18 fr in outside diameter. Slightly downstream of wiper 38 is isolator silicone molded diaphram isolator seal 39 having a centrally located through slit 40. It is also contemplated that wiper 38 and isolator seal 39 can be formed in one unitized silicone molded part and not as separate components.

Seal 39 is slightly press fit into recess 37 such that slit 40 is normally biased sealed shut preventing the escape of any administered pressurized gasses to atmosphere. Injection molded tubular housing 41 has collar 42 which is solvent cemented to recess 37 effectively joining housing 41 to connector 30 and sealing in isolator seal 39. Housing 41 has interior catheter isolator tunnel 43 which houses PVC suction catheter 44 with distal tip opening 45 with side vent hole 46 and black catheter indicator mark 47. Silicone catheter tunnel seal 48 is held in place by solvent bonded fitting 49. The catheter 44 is usually about 22 inches long and is protectively surrounded by thin collapsible polyethylene sleeve 50 which is captured onto fitting 49 by press fit ring 51 and attached to valve 10 by rear ring 52. It should be noted that tubular housing 41 is molded opaque such that once catheter 44 is retracted back into isolator tunnel 43 it is not visible and the black indicator mark is also not visible. Also port 57 has short tubing 53 which terminates in molded housing 54 which encases one-way silicone molded duckbill anti-reflux valve 55. Housing 54 has a luer opening 58 attachable to any fluid vial or syringe. As can be seen, system 29 is formed in one complete unitized system utilizing high efficiency valve 10.

Figure 7:
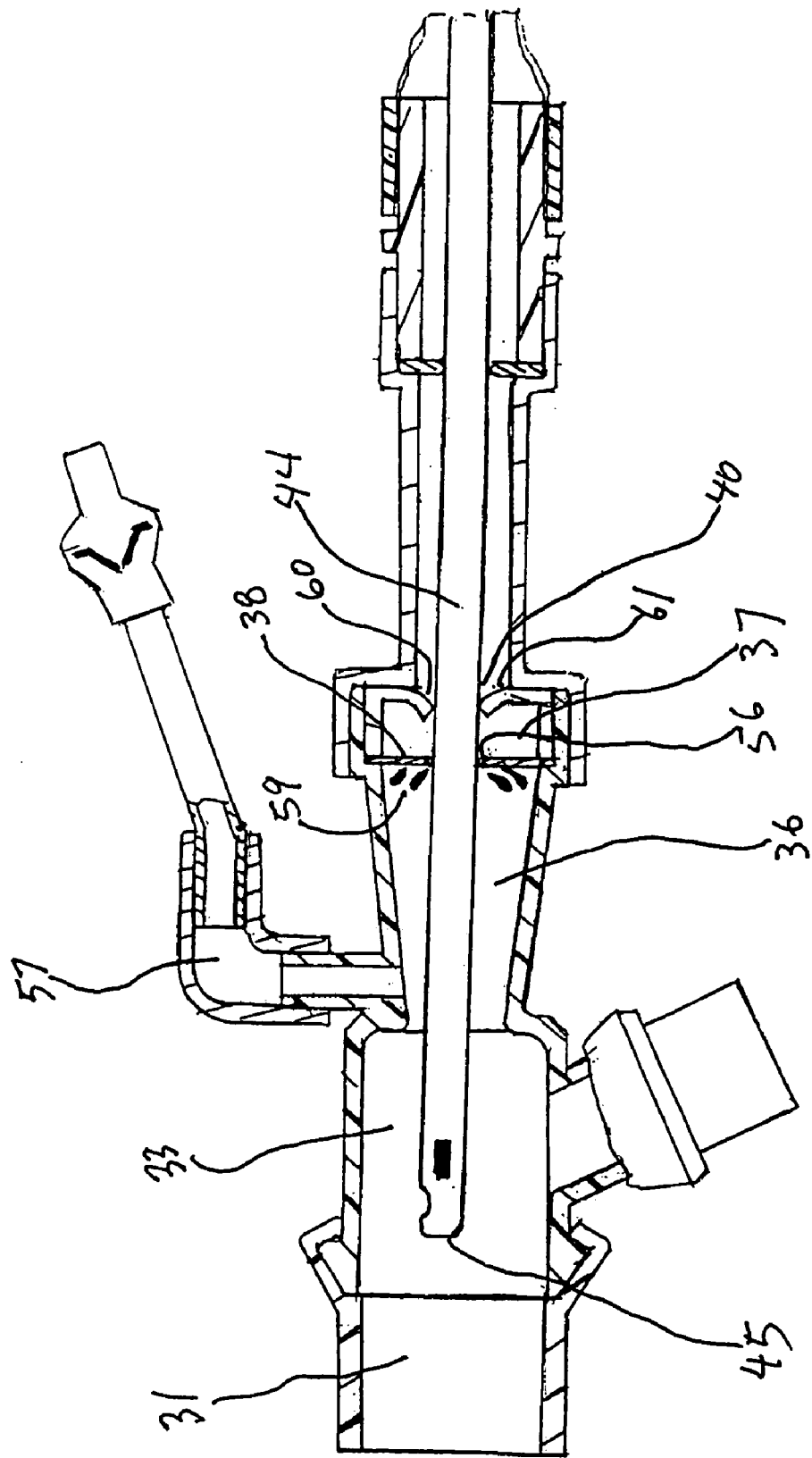
FIG. 7 is an enlarged partial side cross sectional view of the closed tracheal suction system of FIG. 6 showing the suction catheter being withdrawn in the vortex catheter cleaning chamber.

As can be seen in FIG. 7 catheter 44 can be slideably manually advanced and retracted and will solely by itself without any external force acting upon isolator seal 39 open and close slit 40 on isolator seal 39. The catheter 44 once advanced from isolator tunnel 43 will cause slit 40 to open forming resilient flexible leafs 60 and 61 which will purse open and sealably close in an air tight fashion in response to advancement or retraction of the catheter 44 through isolator seal 39. Catheter 44 can be fully advanced through front swivel 31 into a patient's airway. Once fully advanced into the airway, suction is intermittently or continuously applied upon actuation of suction valve 10 as the catheter 44 is being withdrawn back from the airway and back into the passage 33. Secretions 59 will be wiped from the outside of catheter 44 by catheter wiper 38 as the catheter is being fully withdrawn. Since the suction valve 10 is highly efficient at secretion removal within the airway, secretions remaining on the outside of the catheter 44 will be minimal compared to the obstructed suction control valves of the prior art. However, some will accumulate as secretions 59 in front of wiper 38.

Figure 8:
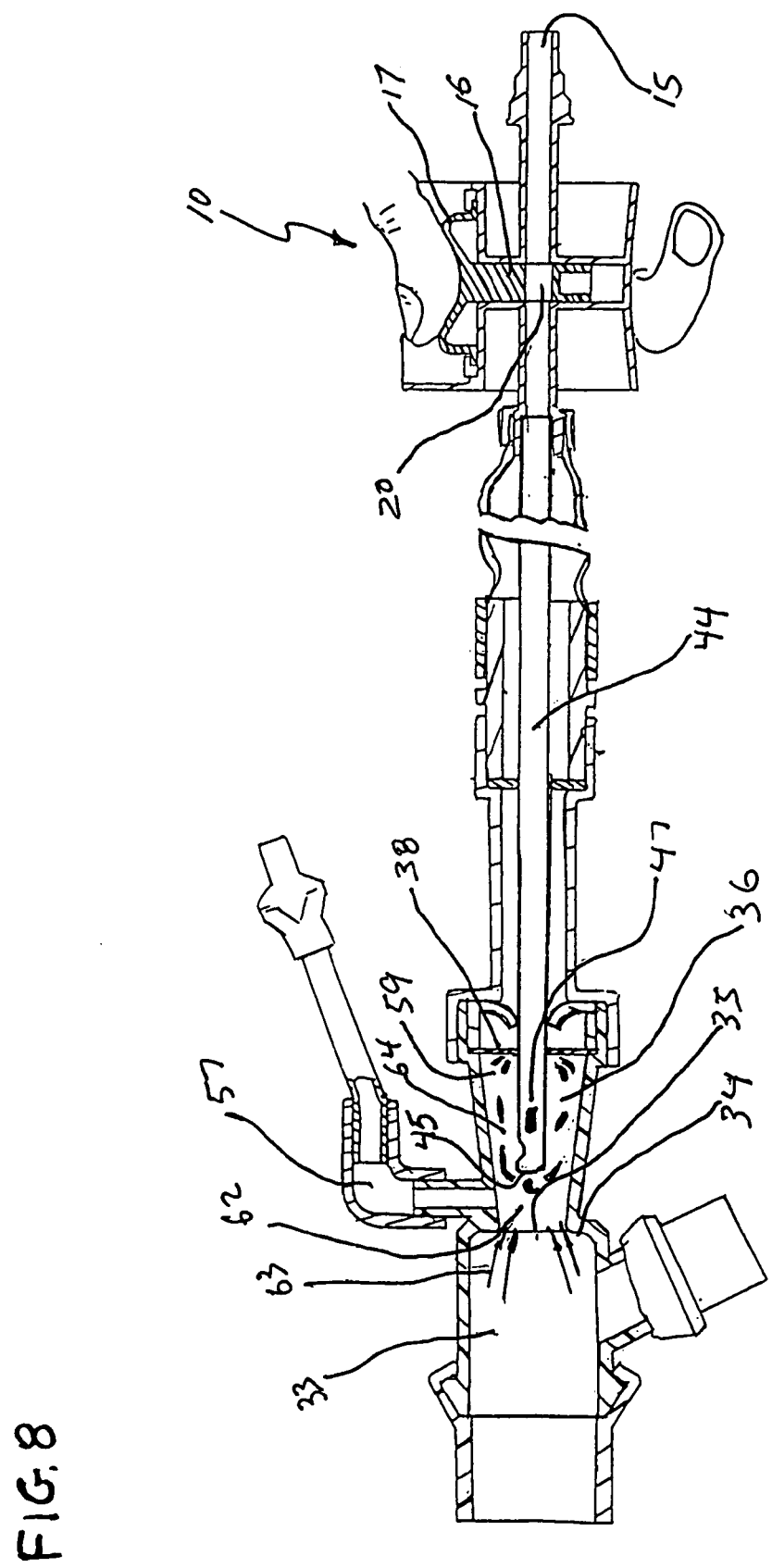
FIG. 8 is a side cross sectional view of the closed tracheal suction system of FIG. 6 showing the vortex action of the catheter cleaning chamber when the catheter is being withdrawn and suction is applied to the distal tip of the catheter by the high efficiency suction control valve.

FIG. 8 depicts catheter 44 being retracted back into catheter cleaning chamber 36 after suctioning such that black mark 47 clearly shows catheter tip 45 located within chamber 36.

Since chamber 36 is progressively funnel shaped, applied suction will provide two actions leading to removal of accumulated secretions 59 from wiper 38. Action one is the creation of a low pressure lift zone 62 at narrow opening 35 which will tend to lift secretions 59 off wiper 38. This low pressure zone 62 is created as air 63 rushes pass narrow opening 35 which will also suck back any secretions left in connector passage 33 in chamber 36. Action two is the creation of a swirling vortex action 64 within cleaning chamber 36 to effectively lift off and remove secretions 59 from wiper 38 and to also clear connector passage 33 of any residual secretions.

Cross lumen 20 on plunger 16 of valve 10 applies full applied suction and air flow to catheter tip 45 creating this dual low pressure zone 62 action and vortex action 64 within chamber 36. All of this dual cleaning action begins to take place to loosen and remove secretions 59 in the direction of catheter tip 45 even before the instillation of flush fluid through port 57. The creation and effectiveness of this dual cleaning action is maximized through the use of the high efficiency suction control valve 10.

Figure 9:
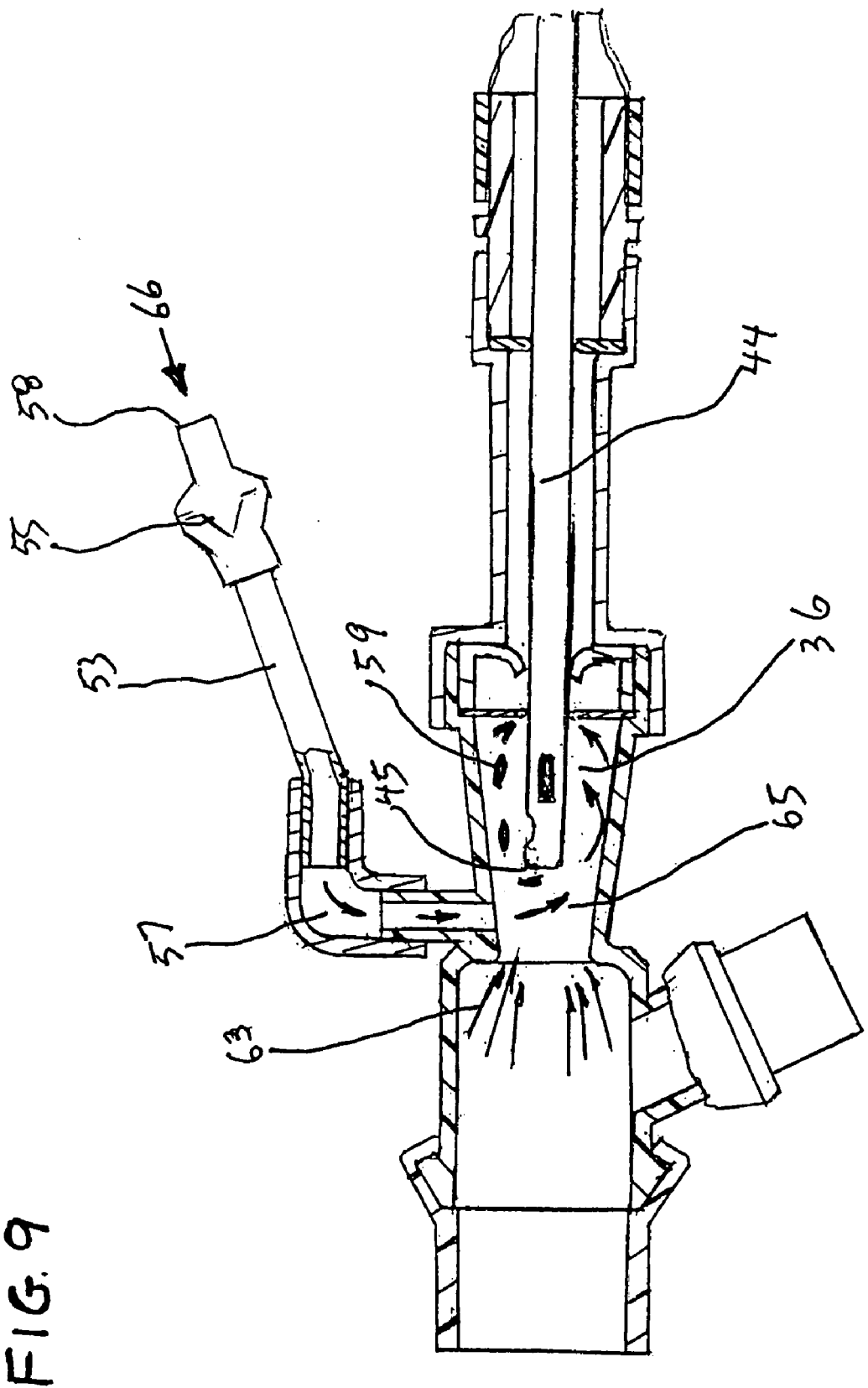
FIG. 9 is a partial side cross sectional view showing the vortex action of the cleaning chamber when used in conjunction with the installation of catheter rinse fluid.

FIG. 9 depicts the instillation of catheter flush fluid 66 into housing 54 which opens duck bill valve 55 by unit dose squeeze vial or 20 cc syringe and instills a swirling rinse liquid air vortex stream 65 in chamber 36 to thoroughly flush and remove secretions 59 as shown. Even the most viscous secretions will be removed within chamber 36 such that essentially no secretions remain which will significantly prevent their reintroduction when the catheter 44 is advanced through chamber 36 upon subsequent suctioning procedures.

Figure 10:
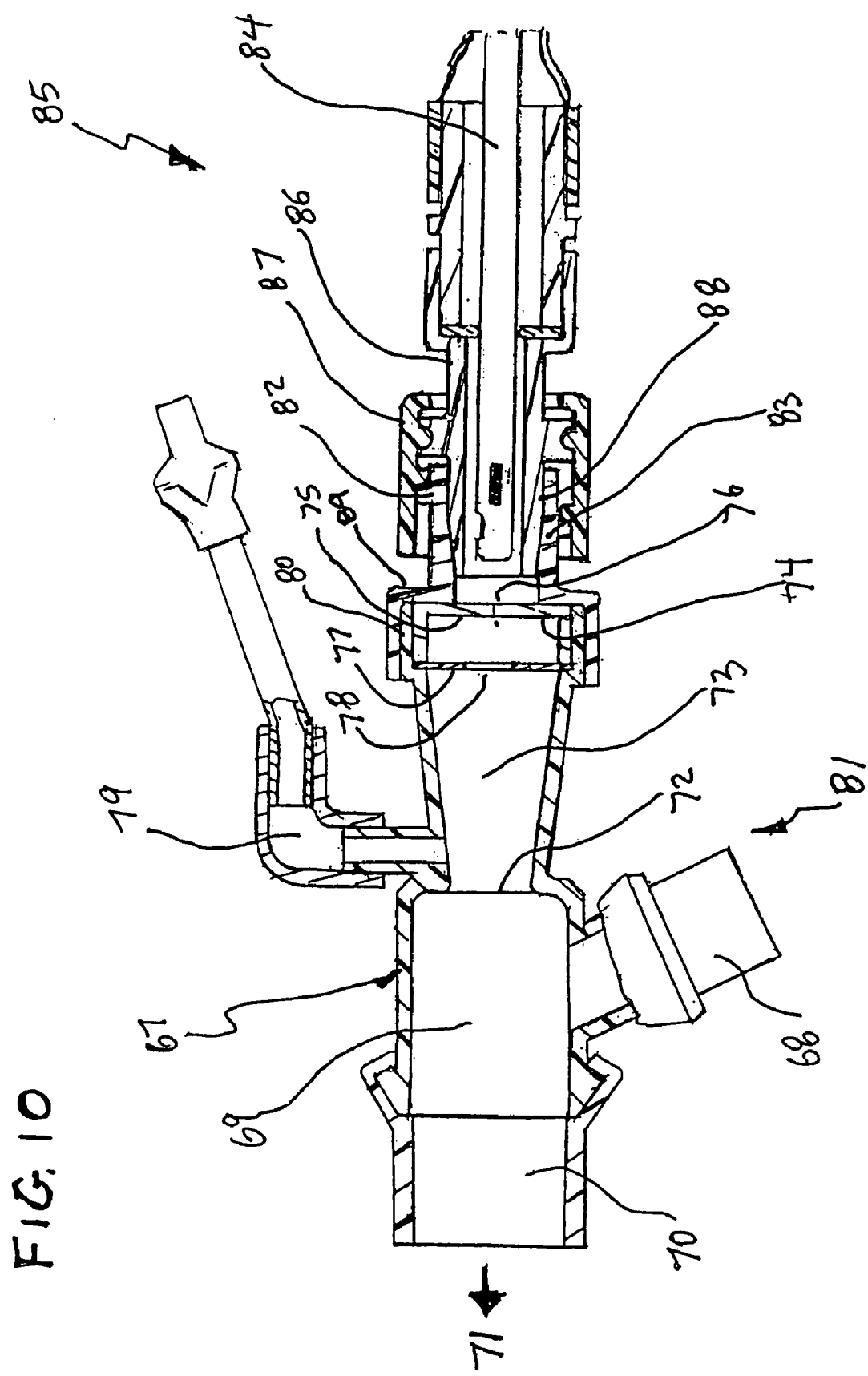
FIG. 10 is a partial side cross sectional view of an alternate embodiment of the closed tracheal suction system shown in FIG. 6 wherein a replaceable catheter cartridge is shown attached to the frontal connector portion of the system.

After catheter cleaning is completed as depicted in FIG. 9 the catheter 44 is fully retracted into isolator tunnel 43 to its original fully 100% isolated position as shown in FIG. 6 wherein catheter 44 is thoroughly clean as well as chamber 36. Seal 39 is 100% positively sealed air tight closed upon full withdrawal of catheter 44 such that passage 33 in connector 30 is completely hermetically sealed off from catheter 44. By comparison the Ballard Trach-Care 72 product which is the commercial embodiment of Crump et. al. U.S. Pat. No. 6,227,200 always leaves the catheter within the front connector air stream since the pivotal flap valve is vented and partially open at all times. This is not the case with the present invention FIG. 10 depicts a slightly alternate embodiment having a frontal manifold 67 configured for delivery of ventilator air to a patient through side swivel 68 into interior air passage 69, out through front swivel 70 into a patient's respiratory system 71. Air passage 69, side swivel 68 and frontal swivel 70 are located at the distal end of manifold 67. Directly adjacent passage 69 is entrance opening 72 leading into catheter cleaning chamber 73. Catheter isolator seal 74 located proximally in the cleaning chamber is molded from silicone rubber and has a thin walled diaphram 75 with slit opening 76 centrally located in diaphram 75. Disposed between entrance opening 72 and isolator seal 74 is very thin walled silicone catheter wiper 77 having central opening 78. Access port 79 permits the delivery of aerosol or liquid fluid into chamber 73 for catheter flushing or the delivery of lavage or medication. Seal 74 and wiper 77 are slightly compression fitted into recess bushing 80 which is solvent cemented into place by threaded collar 89.

In summary this assembly forms a first part swivel manifold 81 which when attached to a ventilator circuit on side swivel 68 and to an airway tube on front swivel 70 is 100% positively sealed from outside atmosphere and from the loss off ventilator air to outside atmosphere by isolator seal 74 which is normally biased to a closed sealed position. Collar 89 has external quarter turn thread 82 and tapered opening 83 forming a channel to isolator seal 74. Elongated suction tube or catheter 84 can open slit 76 solely upon manual contact and insertion of catheter 84 through slit 76 to suction a patient's airway. Retraction of catheter 84 from slit 76 will automatically return seal 74 to its normally sealed closed to atmosphere position. Catheter 84 can be configured to be part of a second part catheter cartridge 85 which can form a coupling relationship with first part swivel manifold 81. Cartridge 85 can have plastic molded catheter guide channel 86 with rotating quarter turn collar 87 which forms an easy to engage and disengage coupling relationship with collar 89 such that taper 88 on channel 86 forms an air tight tapered lock with tapered opening 83 on collar 89. Catheter 84 is normally positioned within channel 86 ready to be advanced or retracted through seal 74. Since seal 74 always remains positively sealed to atmosphere the second part catheter cartridge 85 can be coupled and uncoupled from first part frontal manifold 81 as desired without loss of ventilator air or PEEP to atmosphere. The first part frontal manifold 81 can remain as part of ventilator circuit while replacement cartridges 85 can be coupled to manifold 81 as desired.

The alternate embodiment described in FIG. 10 has all the clinical advantages of the system depicted in FIG. 6 but instead of being completely unitized as FIG. 6 shows, it can be a two part system as shown in FIG. 10 with the catheter cleaning chamber 73 remaining to be a part of manifold 81. The catheter 84 is easily attached to the high efficiency suction control valve of FIG. 2 such that the cartridge 85 can incorporate all the advantages of suction control valve 10 in FIG. 2 and become a two part closed tracheal suction system.

As can be seen, the embodiments described clearly meet the objects of the present invention. Those skilled in the art can readily make various changes in materials, construction, design, and assembly methods without departing from the broad scope and spirit of the present invention.

I claim:

1. A suction catheter system for suctioning secretions from a patient comprising; a connector having an inner air passage with frontal and rearward ends and the connector configured for delivery of ventilator air to and from a patient, a catheter isolator seal disposed at the rearward end of the connector inner air passage, a catheter cleaning chamber including a catheter cleaning flush port located in front of the catheter isolator seal, the isolator seal normally biased to a closed position; a suction catheter assembly associated with both the catheter isolator seal and the catheter cleaning chamber, a catheter assembly having a catheter with a distal tip and a proximal end, said catheter advanceable and retractable through the catheter isolator seal, the catheter isolator seal operable to an open position solely by direct contact and manual advancement of the distal tip of the catheter with the isolator seal.

2. The system of claim 1 wherein the isolator seal is normally biased to a sealed position to substantially prevent the loss of ventilator air out the seal.

3. The system of claim 1 wherein the cleaning chamber includes a catheter wiper.

4. The system of claim 1 wherein the catheter isolator seal is a resiliently molded component.

5. The system of claim 1 including a catheter isolation tunnel located behind the catheter isolator seal.

6. The system of claim 1 wherein the catheter assembly is fixedly attached to both the catheter isolator seal and the catheter cleaning chamber.

7. The system of claim 1 wherein the catheter assembly is disconnectable from the catheter isolator seal and the catheter cleaning chamber.

8. The system of claim 1 wherein the catheter cleaning flush port permits the instillation of fluid.

9. The system of claim 1 wherein the catheter cleaning port includes a one-way valve.

10. The system of claim 1 wherein the catheter isolator seal has a slit opening normally biased to a closed position.

11. The system of claim 1 wherein the catheter is enclosed in a collapsible sleeve.

12. The system of claim 1 wherein the catheter is connectable to a source of suction.

13. The system of claim 1 wherein the catheter is attached to a suction control valve.

14. A suction catheter system for suctioning secretions from a patient comprising; a connector having front and rear ends and configured for delivery of ventilator air to and from a patient, a catheter isolator wiper seal disposed at the rear end of the connector, a catheter cleaning chamber including a catheter cleaning flush port located in front of the catheter isolator wiper seal, the catheter isolator wiper seal normally biased to a closed position, a suction catheter assembly operably associated with both the catheter isolator wiper seal and the catheter cleaning chamber, said suction catheter assembly having a catheter with a distal tip, said catheter advanceable and retractable through the catheter isolator wiper seal, the catheter isolator wiper seal operable to an open position solely by direct contact and manual advancement of the distal tip of the catheter with the catheter wiper seal.

15. The system of claim 14 wherein a catheter isolation tunnel is positioned behind the catheter isolator wiper seal.

16. The system of claim 14 wherein the suction catheter system is a closed tracheal suction system.

17. The system of claim 14 wherein the catheter isolator seal and the catheter wiper function as one component.

18. The system of claim 14 wherein the catheter isolator seal and the catheter wiper function as separate components.

19. The system of claim 18 wherein the catheter wiper is positioned in front of the catheter isolator seal.

20. A suction catheter system for removing secretions from a patient's airway comprising; a catheter assembly including an isolation tunnel and having a catheter with a distal tip and proximal end, the distal tip normally positioned within said isolation tunnel and the proximal end of the catheter connectable to an applied suction source, a catheter isolator wiper seal located in front of the catheter isolation tunnel and a catheter cleaning chamber including a catheter cleaning flush port located in front of the catheter isolator wiper seal, a connector for delivery of ventilator air to and from a patient located in front of the catheter cleaning chamber and catheter cleaning flush port, the catheter distal tip advanceable and retractable into a patient's airway through the catheter isolator wiper seal from its normal position within the isolation tunnel, where the catheter is wiped of secretions upon retraction back through the catheter isolator wiper seal and said secretions accumulate in the catheter cleaning chamber located in front of the catheter isolator wiper seal, and wherein said accumulated secretions are removed from the catheter cleaning chamber by the instillation of catheter flush fluid through the port and into the catheter cleaning chamber during the application of suction through the catheter when the catheter tip is positioned within the catheter cleaning chamber.

* * * * *